(12) United States Patent  (10) Patent No.: US 7,667,184 B2
Noguchi et al.  (45) Date of Patent: Feb. 23, 2010

(54) OPTICAL INFORMATION READER

(75) Inventors: Masahisa Noguchi, Ichihara (JP); Ken Tsukii, Tokyo (JP); Hideji Tajima, Matsudo (JP)

(73) Assignees: Percision System Science Co., Ltd., Matsudo-shi, Chiba (JP); Furukawa Electric Co., Ltd., Chiyoda-ku, Tokyo (JP); Furukawa Electric Advanced Engineering Co., Ltd., Ichihara-shi, Chiba (JP)

( * ) Notice: Subject to any disclaimer, the term of this patent is extended or adjusted under 35 U.S.C. 154(b) by 78 days.

(21) Appl. No.: 11/568,384

(22) PCT Filed: Apr. 28, 2005

(86) PCT No.: PCT/JP2005/008155

§ 371 (c)(1),
(2), (4) Date: Jun. 15, 2007

(87) PCT Pub. No.: WO2005/106433

PCT Pub. Date: Nov. 10, 2005

(65) Prior Publication Data

US 2007/0278383 A1  Dec. 6, 2007

(30) Foreign Application Priority Data

Apr. 30, 2004  (JP)  ............................. 2004-136239

(51) Int. Cl.
*G06M 7/00*  (2006.01)
*G01J 1/04*  (2006.01)
*G01N 21/01*  (2006.01)
*G02B 6/00*  (2006.01)

(52) U.S. Cl. .................. 250/221; 250/227.14; 356/244; 385/12

(58) Field of Classification Search .............. 250/201.3, 250/201.4, 201.5, 221, 216, 227.14–227.19, 250/227.23, 573–577, 559.06; 356/244, 356/246, 446; 385/5, 12, 32
See application file for complete search history.

(56) References Cited

U.S. PATENT DOCUMENTS 5,445,994 A  8/1995  Gilton (Continued)

FOREIGN PATENT DOCUMENTS

JP  7-159407  6/1995

(Continued)

*Primary Examiner*—Georgia Y Epps
*Assistant Examiner*—Don Williams
(74) *Attorney, Agent, or Firm*—Haynes and Boone, LLP

(57) ABSTRACT

The invention aims to provide an optical information reader which can identify precisely, reliably, and with high sensitivity, even when the quantity or the wavelength of light from a measuring object from which optical information is to be read, extends over a wide range. The optical information reader comprises: a substrate on which one or more biological materials labeled by a combination of presence or extent of a plurality of kinds of optical labeling elements are immobilized at one or more different immobilized positions; one or more light-receiving ends capable of receiving light from the substrate; an optical information measuring unit which obtains optical information on a specific measuring object on the substrate based on an electric signal obtained by converting the light received by the light-receiving end by photoelectric elements having different characteristics determined depending on the measuring object; and a scanning unit which scans the substrate by moving the substrate and the light-receiving end relative to each other, and the optical information measuring unit has an optical waveguide.

20 Claims, 7 Drawing Sheets

U.S. PATENT DOCUMENTS 5,744,305 A     4/1998  Fodor et al.
6,853,454 B1 *  2/2005  Heffelfinger ................ 356/446

FOREIGN PATENT DOCUMENTS

| JP | 9-502273     | 3/1997 |
| JP | 2001-41891   | 2/2001 |
| JP | 2002-243641  | 8/2002 |
| JP | 2003-107083  | 4/2003 |
| WO | WO 00/05357  | 2/2000 |
| WO | WO 00/43751  | 7/2000 |

* cited by examiner

OPTICAL INFORMATION READER

CROSS REFERENCE

This application is a United States national phase application of co-pending international patent application number PCT/JP2005/008155, filed Apr. 28, 2005, which claims priority to Japanese patent application number 2004-136239, filed Apr. 30, 2004 which priority is claimed.

TECHNICAL FIELD

The present invention relates to an optical information reader. More specifically, the present invention relates to an optical information reader for reading optical information from an optical labeling element or the like coupled with a biological material, in order to analyze structures and properties of various biological materials, or to check for the presence of biological materials.

BACKGROUND ART

Conventionally, an analysis method using a substrate such as a DNA chip, on which biological materials having a known chemical structure are arranged and immobilized in a plurality of positions, has been used extensively. In this analysis method, a solution in which a target biological material having an unknown chemical structure and labeled by a fluorescent material or the like is suspended, is brought into contact with the substrate such as the DNA chip, so that the target biological material and the known biological material are coupled and reacted with each other, thereby analyzing the chemical structure of the target biological material from a detected position of the labeling material. In order to perform the analysis, it has been necessary to reliably capture faint luminescence from the labeling material such as the fluorescent material of the molecular level, coupled with the biological materials immobilized on the substrate such as the DNA chip.

For this purpose, it is necessary to multiply the received faint light by using a photomultiplier (PMT), to convert the light to an electric signal that can be subjected to information processing (Foreign Patent Documents 1 and 2).

Patent Document 1: U.S. Pat. No. 5,445,994
Patent Document 2: U.S. Pat. No. 5,744,305

DISCLOSURE OF THE INVENTION

Problems to be Solved by the Invention

Recently, the need of labeling for enabling identification of various kinds of target biological materials is increasing in order to determine or analyze a base sequence of DNA and the structure of the biological material such as protein. In order to label various kinds of target biological materials, a labeling method has been disclosed, in which not only a plurality of different kinds of labeling materials is used, but also the ratio of quantity (mass ratio and molecular weight ratio) is specified to perform labeling, taking into consideration that the kind of substance suitable for labeling is limited (PCT International Publication No. WO 00/5357 by Masayuki MACHIDA et. al). When labeling is performed by using such a ratio of quantity, if the kind of the target biological material is different, the quantity of light from a measuring object becomes different, and the quantity of light to be received is distributed to a certain wide range. Moreover, even when labeling is performed without using the ratio of quantity, the quantity of the biological materials on the DNA chip, the quantity of the labeled target biological material to be coupled therewith, and the quantity of the labeling material for labeling the target biological material are determined within a range of statistical error, and cannot be always determined to a certain quantity, and an unpredictable quantity of light may be received.

However, there is a limitation on the quantity that the photomultiplier can convert to an electric signal, and if the range of the acceptable quantity of light is taken widely, a multiplication factor thereof should be suppressed to be low, thereby causing a problem in that the electric signal cannot be obtained with high sensitivity. Moreover, since it is necessary to know the immobilized positions of the optical labeling elements, such as the luminescence thereof, on the DNA chip, the substrate itself needs to be measured as a measuring object, and hence, the measuring object is not limited to the optical labeling elements. Since the objects other than the labeling elements do not emit light, the received quantity of light does not change as much as expected, but the range of the wavelength of light to be received is obviously different.

Thus, there is a measuring object having a narrow range, in which emission intensity, emission quantity, reflection quantity, emission wavelength, reflection wavelength, size of the object, measurement accuracy, and measurement purpose are determined, and a measuring object having a wide range thereof, and in order to perform accurate and precise analysis of the target biological material by using the DNA chip, these measuring objects need to be handled separately.

The present invention has been achieved in order to solve the above problems, and it is a first object of the present invention to provide an optical information reader which can identify various kinds of optical labeling elements immobilized on the substrate precisely, reliably, and with high sensitivity, when the ratio of quantity of light is used for labeling and even when the quantity or the wavelength of light from the measuring object extends over a wide range.

It is a second object of the present invention to provide an optical information reader which: can flexibly perform various types of processing such as precise inspection using the substrate, even when immobilization of the substrate and the biological materials, and the labeling extent such as emission intensity are not strictly standardized, for example, when there is a difference in the spotting size and a density difference of the biological materials, at the immobilized positions of respective biological materials on the substrate; can increase the types of usable substrates and usable labeling materials; and can reduce the labor and cost for manufacturing or inspection.

It is a third object of the present invention to provide an optical information reader which can perform sound and reliable reading, while suppressing an adverse effect on receiving of light due to irradiation of pump light.

It is a fourth object of the present invention to provide an optical information reader having flexibility or diversity which can flexibly correspond to a processing object.

Means for Solving the Problems

The present invention has been achieved in order to solve the above problems, and a first aspect of the invention is an optical information reader comprising: a substrate on which one or more biological materials labeled by a combination of presence or extent of a plurality of kinds of optical labeling elements are immobilized at one or more different immobilized positions; one or more light-receiving ends capable of receiving light from the substrate; an optical information measuring unit which obtains optical information on a specific measuring object on the substrate based on an electric signal obtained by converting the light received by the light-receiving end by a photoelectric element, which performs photoelectrical conversion according to different characteristics determined depending on the measuring object; and a scanning unit which scans the substrate by moving the substrate and the light-receiving end relative to each other, and the optical information measuring unit has an optical waveguide.

Here, the "optical labeling element" is an element capable of labeling a solid body or substance coupled with the optical labeling element by emitting, reflecting, scattering, or absorbing light. For example, the one labeling by emitting light includes luminescent materials such as a fluorescent material, a phosphorescent material, and a chemiluminescent material. The one labeling by reflecting light includes, for example, a substance having a high reflectivity using a metal surface, and the one labeling by absorbing light includes, for example, a dye and a pigment.

The "substrate" is a solid body on which various kinds of biological materials, whose structure is known or unknown, are immobilized at predetermined positions, and the biological material can be specified by measuring the position on the solid body. Particularly, the substrate is brought into contact with a solution, in which a target biological material having a possibility of being coupled with the biological materials is labeled by coupling it with the optical labeling element and suspended, and is then washed, and it is determined whether the target biological material is coupled with the biological materials on the substrate, and if it is coupled therewith, the position of the coupling on the substrate is measured by detecting the optical labeling element. There is no limitation on the shape of the substrate, and the substrate includes DNA chips of a plate shape, a thin film shape, a string shape, and a filamentous shape. The biological materials are, for example, genetic materials such as DNA, RNA, mRNA, oligonucleotides, and nucleotides, proteins, amino acids, antigens, antibodies, and sugar chains.

The "measuring object" is an object to be measured to obtain optical information, and for example, is the substrate itself required for detecting the immobilized position, respective biological materials immobilized on the substrate, the optical labeling element, and a marker as a reference of position on the substrate. Alternatively, the measuring object is a specific labeling material in the optical labeling element.

The "specific measuring object" is at least one measuring object of a plurality of measuring objects relating to the substrate, being one with the quantity of light of the specific object being distributed over a wide range. The measuring object is, for example, an optical labeling element used for labeling by making the ratio of quantity of a plurality of kinds of optical labeling elements different from each other, being an object where the quantity of light obtained from the optical labeling elements is not always constant on respective positions on the substrate.

"Depending on the specific measuring object" means taking into consideration, for example, the emission intensity, reflected light intensity, emission wavelength, wavelength of reflected light, absorption wavelength, absorption intensity, emission lifetime, emission timing of the measuring object, the size of the measuring object, the shape of the measuring object, necessity of measurement accuracy of the measuring object, and a measurement purpose.

The "photoelectric element which performs photoelectrical conversion according to different characteristics" means that there is a case in which a plurality of characteristics can be set for one photoelectric element or a plurality of photoelectric elements of the same kind, and a case in which a plurality of photoelectric elements of different kinds having different characteristics is used. The "photoelectric element" stands for an electron element using a photoelectric effect, and includes, for example, a photoelectric tube, a photomultiplier, a photoconductive cell, a photodiode, and a photo transistor. The photoelectric element generally outputs an electric signal of a predetermined size corresponding to the intensity of light, only in the case of a range in which there is the intensity of light input by the photoelectric element. The "characteristic" stands for a functional relation between the intensity of input light and the intensity of the output electric signal when the received light is converted to the electric signal. The photoelectric element corresponds to a light receiving unit for an irradiation unit described later.

The "optical waveguide" stands for a circuit or a line for transmitting the light by confining the light in a certain area, and includes not only an optical fiber but also a plate-like waveguide and a thin-film waveguide. The "light-receiving end" refers to a part in which the light from the measuring object such as the substrate enters. For example, an end or an end face of the optical fiber, or a head having an optical system such as a lens corresponding thereto.

According to the first aspect of the invention, a photoelectric element having a different characteristic dependent on the measuring object is provided for the specific measuring object, and optical information on the measuring object is obtained by converting the light received by the light-receiving end into an electric signal according to respective characteristics. Therefore, even when the quantity of light or wavelength of the light from the measuring object is distributed over a wide range, the input quantity of light can be determined by obtaining an electric signal based on a predetermined functional relation corresponding to the input quantity of light, from amongst electric signals converted by the photoelectric element which performs photoelectric conversion by using a plurality of characteristics. Accordingly, optical information on the measuring object can be obtained accurately and reliably with high sensitivity, over a wide range.

Moreover, even when the substrate and the like are not strictly standardized, for example, when there is a difference in the size of the measuring object and a density difference of the biological materials, at the immobilized positions of respective biological materials on the substrate, various types of processing such as precise inspection using the substrate can be performed flexibly, thereby increasing the types of usable substrates and usable labeling materials, and enabling a reduction in the labor and cost for manufacturing or inspection. Accordingly, there is an advantage in that an optical information reader having flexibility or diversity which can flexibly correspond to a processing object can be provided.

A second aspect of the invention is an optical information reader, in which the photoelectric element is a plurality of photomultipliers, for which multiplication factors different from each other corresponding to a specific measuring object on the substrate are set, and the optical information measuring unit has a light distribution unit which extracts light having a wavelength range corresponding to the measuring object from amongst the light from one light-receiving end, and distributes the light to each photomultiplier.

The "light distribution unit" includes, for example, a filter for transmitting only light of a corresponding wavelength range of the light from the light-receiving end, and a branching unit which branches the light transmitted through the filter to a plurality of branched paths.

According to the second aspect of the invention, a plurality of photomultipliers is used, for which multiplication factors different from each other are set. As a result, photomultipliers having various multiplication factors are provided for the specific measuring object, for example, a fluorescent material used for labeling according to a difference of ratio of quantity, thereby enlarging the range of the quantity of light of the measuring object and enabling measurement with high sensitivity in a wide range.

A third aspect of the invention is an optical information reader, in which the optical information measuring unit comprises; a connector detachably connected to the light-receiving end via the optical waveguide, and a light extraction unit which extracts a wavelength range corresponding to the measuring object, and the photoelectric element is one or more photomultipliers, for which a multiplication factor corresponding to the measuring object on the substrate is set.

According to the third aspect of the invention, the optical information measuring unit is provided detachably connected to the light-receiving end via the optical waveguide. Consequently, the optical information measuring unit can be added so as to perform measurement with respect to various measuring objects, without increasing the apparatus size, by replacing the light-receiving end thereby via the optical waveguide. Moreover, the optical information measuring unit can correspond flexibly to an increase in the measuring objects.

A fourth aspect of the invention is an optical information reader, in which the optical labeling element includes one which emits light by irradiating pump light, and the optical information measuring unit has an irradiation unit which irradiates the pump light onto the substrate.

Here, for the optical labeling element, a fluorescent material or a phosphorescent substance is considered.

According to the fourth aspect of the invention, by enabling irradiation of the pump light, the invention can be applied also to a case in which the optical labeling element is a fluorescent material or a phosphorescent substance.

A fifth aspect of the invention is an optical information reader, in which a light-receiving direction and an angular aperture of the light-receiving end relative to the substrate is set so that the light-receiving end receives light from the substrate, outside of an incident route and a reflection route of the pump light determined based on an irradiation direction and an illuminating angle of the irradiation unit relative to the substrate, and a shape of the substrate.

According to the fifth aspect of the invention, since the pump light is not received directly nor indirectly by the light-receiving end, highly reliable measurement can be performed.

A sixth aspect of the invention is an optical information reader, in which the optical information measuring unit recognizes the shape of the substrate based on the light both from the optical labeling elements on the substrate and the substrate itself, as the measuring objects, received by the light-receiving end.

According to the sixth aspect of the invention, as the measuring objects, not only the optical labeling element is simply selected, but also the substrate itself is designated as the measuring object. As a result, the positions of the measured optical labeling elements can be specified reliably.

A seventh aspect of the invention is an optical information reader, in which the substrate or the light-receiving end rotates relatively to an axis passing through the center of the substrate, and also moves relatively to the axial direction, thereby spirally scanning a measurement area to be measured by the optical information measuring unit, to obtain the optical information.

According to the seventh aspect of the invention, since the substrate or the light-receiving end rotates relatively to the axis passing through the center of the substrate, and also moves relatively to the axial direction, the measurement area is scanned spirally. Accordingly, even if the immobilized positions of the biological materials arranged on the substrate are three-dimensional, respective immobilized positions can be scanned so as to cover all the immobilized positions reliably.

An eighth aspect of the invention is an optical information reader in which the scanning unit scans the substrate based on the specified shape of the substrate, and the optical information measuring unit obtains the optical information based on the specified shape of the substrate.

According to the eighth aspect of the invention, since scanning is performed based on the shape of the substrate, scanning can be performed so as to reliably pass through the immobilized positions of the biological materials immobilized on the substrate. As a result, the positions of the respective biological materials can be specified reliably and easily. Moreover, according to the eighth aspect of the invention, since the shape of the substrate need not be recognized, a shape recognition process can be omitted, thereby enabling easy and high-speed processing.

A ninth aspect of the invention is an optical information reader in which the scanning unit scans along a predetermined route set on the substrate, and the optical information measuring unit obtains the optical information based on the order of scanning of the optical labeling elements.

Here the "predetermined route" is a route, for example, preset so as to cover respective immobilized positions on the substrate, including straight, multilinear, curved, spiral, zig-zag, and curled shapes.

According to the ninth aspect of the invention, by scanning along a predetermined route on the substrate, for example, a route sequentially covering the immobilized positions on the substrate, the biological materials can be specified based on the order of the immobilized positions thereof without measuring a coordinate position on the substrate. As a result, analysis is further facilitated.

A tenth aspect of the invention is an optical information reader in which the scanning unit comprises a synchronization unit which applies vibrations based on a characteristic frequency of the substrate and a characteristic frequency of the light-receiving end to one of the substrate or the light-receiving end, so that the one follows the other, thereby making a difference between the characteristic frequencies thereof equal to or less than a predetermined value.

According to the tenth aspect of the invention, by providing the scanning unit with the synchronization unit which applies vibrations based on the characteristic frequency of the substrate and the characteristic frequency of the light-receiving end, to one of the substrate or the light-receiving end, so that the one follows the other, thereby making a difference between the characteristic frequencies thereof equal to or less than a predetermined value, relative blurring between the light-receiving end and the substrate due to vibrations is removed, thereby enabling accurate position measurement of the measuring objects on the substrate.

An eleventh aspect of the invention is an optical information reader, in which the synchronization unit has a positioning part coming in contact with the substrate and the light-receiving end.

Here, "contact" includes a case in which the positioning part comes in direct contact with the substrate and the light-receiving end, and a case in which the positioning part comes in indirect contact with the substrate and the light-receiving end. For example, there is a case in which the positioning part comes in contact with the substrate and the light-receiving end, when the substrate is fixed in a container and stored therein.

According to the eleventh aspect of the invention, by providing the positioning part as the synchronization unit, the substrate and the light-receiving end are brought into direct or indirect contact with each other, to remove relative blurring, thereby enabling accurate position and shape measurement.

A twelfth aspect of the invention is an optical information reader, in which the positioning part comprises a rotor.

According to the twelfth aspect of the invention, the same effect as that of the eleventh aspect of the invention can be obtained. Particularly, according to the twelfth aspect of the invention, at the time of direct or indirect contact with the substrate, friction between the contacting bodies can be reduced, enabling smooth scanning.

A thirteenth aspect of the invention is an optical information reader, in which the optical information measuring unit measures the substrate and the optical labeling elements of the biological materials individually.

Here, the reason why these are "individually" measured is that since the light from the substrate itself, for example, the reflected light, and the light from the optical labeling elements, for example, the fluorescence have generally different quantity and intensity of light, by receiving the light by separate photoelectric elements matched with the respective lights, the optical information can be obtained more clearly.

According to the thirteenth aspect of the invention, by individually measuring the substrate itself and the optical labeling elements as the measuring objects, measurement can be performed by using a photoelectric element having an optimum characteristic corresponding to the property and the shape of the substrate and the property and the size of the optical labeling elements. As a result, accurate optical information can be obtained.

A fourteenth aspect of the invention is an optical information reader, in which an illuminating angle formed between the optical axis of the irradiation unit and a normal at a measuring position on the substrate is larger than an angular aperture of the light-receiving end relative to the measuring position on the substrate.

According to the fourteenth aspect of the invention, since the pump light is not received by the light-receiving end directly or indirectly, highly reliable measurement can be performed.

A fifteenth aspect of the invention is an optical information reader, comprising a container for storing the substrate together with liquid, wherein receiving of light from the substrate by the light-receiving end is performed in a state with the substrate being stored in the container together with the liquid.

Here, the "container" is one capable of collecting the liquid, and includes a normal container, as well as one having an input/output port of the liquid or having a liquid passage, for example, a pipette tip.

According to the fifteenth aspect of the invention, receiving of light from the substrate by the light-receiving end is performed in a state with the substrate being stored in the container together with the liquid, thereby enabling processing and measurement of the substrate in the same container. As a result, the processing can be automated coherently. Moreover, since the substrate is measured in the liquid, correction of the measurement results for droplets adhered to the substrate, and removal of the droplets need not be performed, and highly reliable measurement result can be easily obtained.

A sixteenth aspect of the invention is an optical information reader, in which light between the optical information measuring unit and the optical labeling element or the substrate is transmitted without penetrating the container.

According to the sixteenth aspect of the invention, the light between the optical information measuring unit and the measuring object such as the optical labeling element or the substrate is transmitted without penetrating the container. As a result, since it is not necessary to take into consideration, attenuation, refraction, or distortion of light due to a wall of the container, or a defect or dirt on the wall, highly reliable measurement results can be obtained.

A seventeenth aspect of the invention is an optical information reader in which the irradiation unit irradiates light using an optical system at the light-receiving end.

According to the seventeenth aspect of the invention, since the irradiation unit irradiates light using the optical system the same as that of the light-receiving end, the number of parts can be reduced, and the manufacturing cost can be reduced.

An eighteenth aspect of the invention is an optical information reader, in which the immobilized positions of respective biological materials on the substrate are arranged according to a predetermined positional rule.

Here the "positional rule" is, for example; being in a matrix shape, having equal intervals, being in a concentric circular shape, or having equal angles.

According to the eighteenth aspect of the invention, since the immobilized positions of respective biological materials on the substrate are arranged according to the predetermined positional rule, by measuring a distance or the like from a reference point, positions for emissions or the like due to the optical labeling elements can be measured.

A nineteenth aspect of the invention is an optical information reader in which the optical waveguide of the optical information measuring unit is an optical fiber which transmits the light between the light-receiving end and the optical information measuring unit.

According to the nineteenth aspect of the invention, since the light from the light-receiving end is guided by using the optical fiber, the light from the substrate or the optical labeling elements can be transmitted substantially without loosing the intensity. As a result, the optical information can be obtained reliably.

A twentieth aspect of the invention is an optical information reader in which the light-receiving end is provided so as to penetrate the container and reach the inside or the inner wall of the container.

According to the twentieth aspect of the invention, since the light from the substrate is received not by penetrating the container, but by the light-receiving end provided so as to penetrate the container, highly reliable measurement can be performed without being affected by the attenuation, refraction, or distortion of light at the time of penetrating the container, or by dirt.

BEST MODE FOR CARRYING OUT THE INVENTION

Embodiments of the present invention will be specifically described below.

First Embodiment

Figure 1:
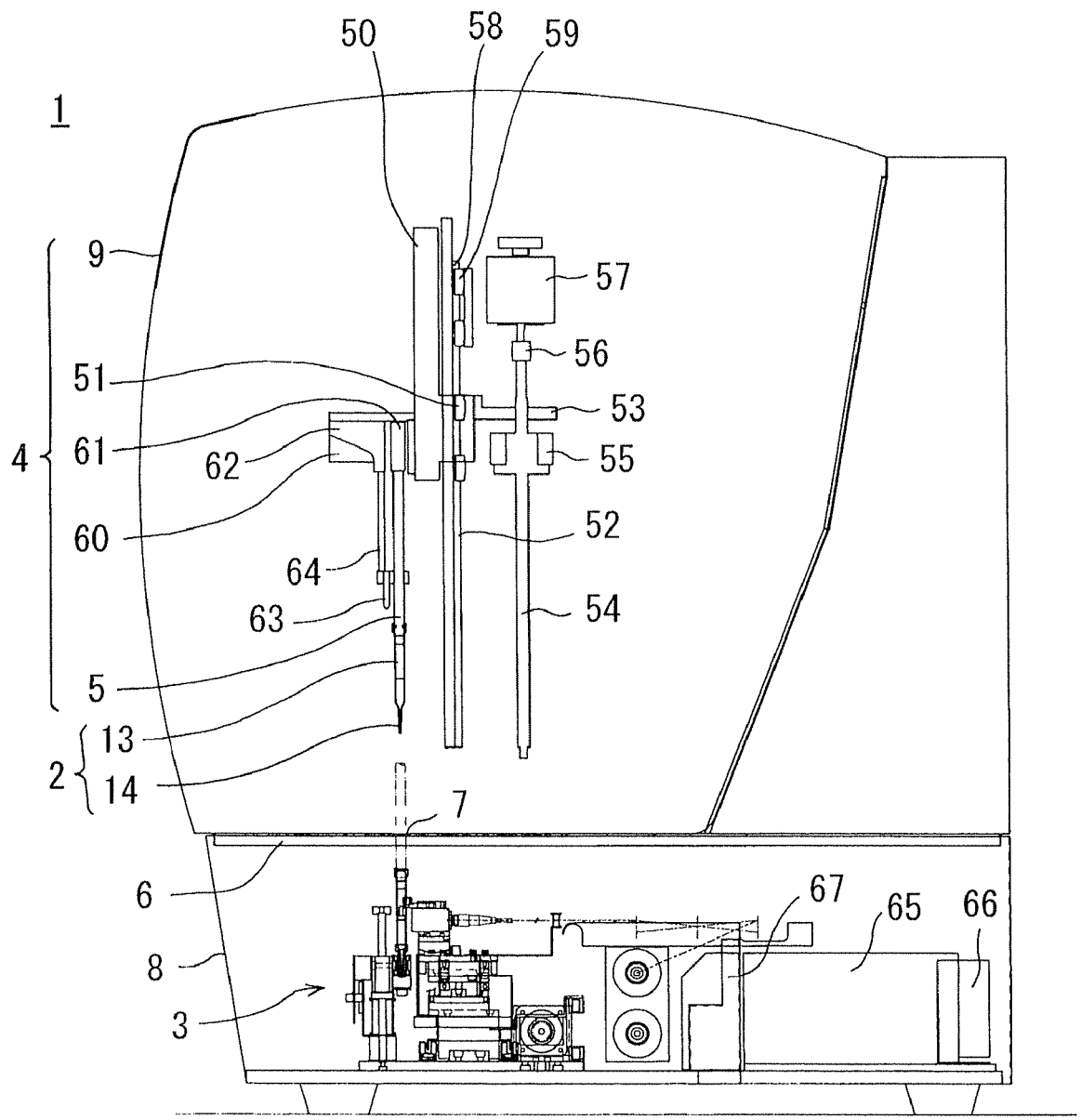
FIG. 1 is an overall diagram of an optical information reader according to an embodiment of the present invention.

FIG. 1 is a front elevation showing an overall optical information reader 1 according to a first embodiment of the present invention.

The optical information reader 1 roughly includes: a plurality of pipette tips 2 (only one is shown in the figure) (for example, six pipette tips are arranged in the vertical direction in the figure) as containers made of a translucent or semitranslucent material, for example, glass, acrylic resin, polyethylene, and polypropylene, capable of storing a substrate, being an object from which optical information is to be obtained; an optical information reader 3 for reading the optical information; and a mechanical section 4 including a rotation scanning unit which makes the pipette tips 2 rotate about an axis thereof for scanning the substrate to obtain the optical information from the substrate, a Z-axis moving unit or XY-axis moving unit (not shown) which makes the pipette tips 2 and the substrate move in the vertical direction or the horizontal direction for measuring the pipette tips 2 and processing the substrate, and a pressure adjusting unit which adjusts the pressure in the pipette tips 2.

Figure 3:
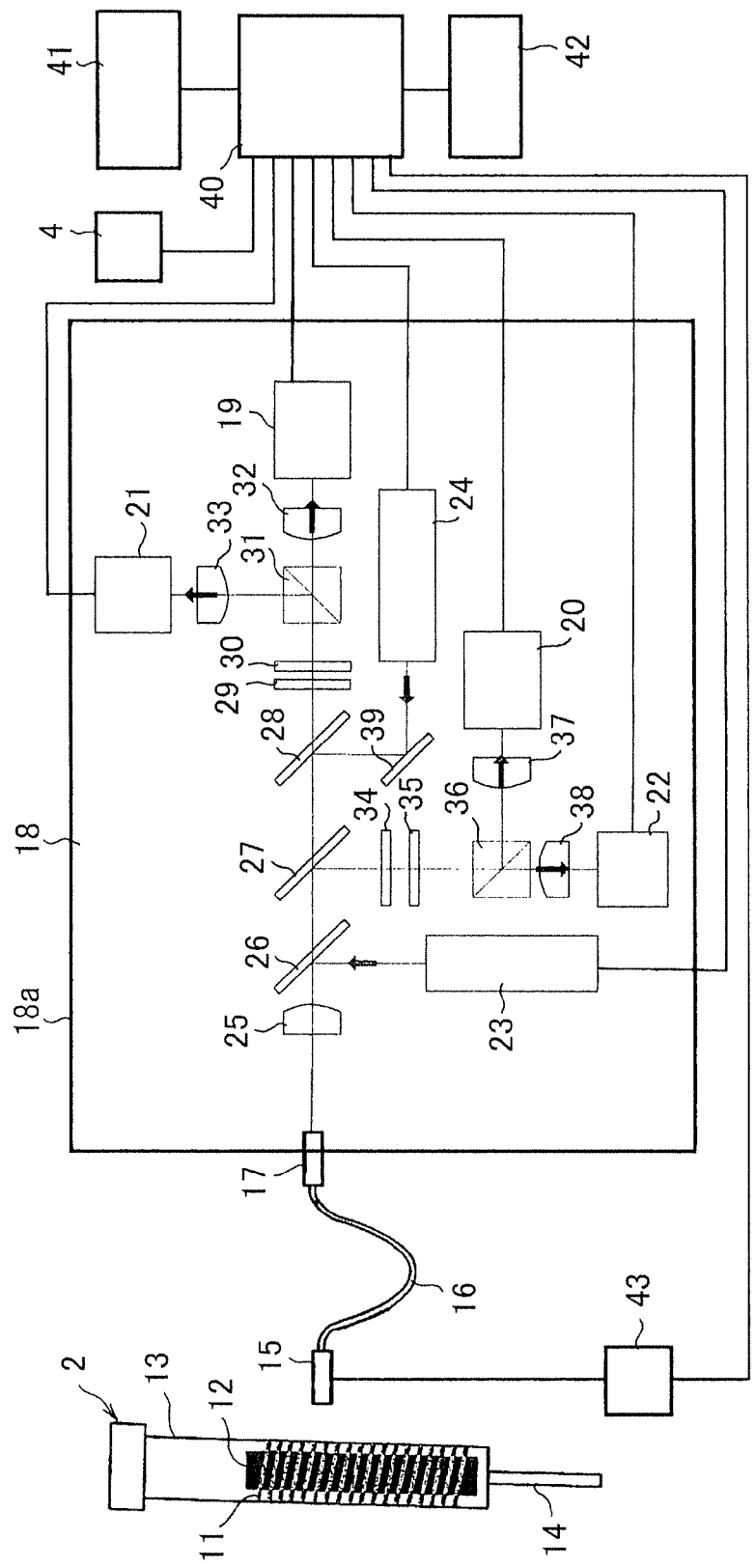
FIG. 3 is a conceptual diagram showing an optical system using a first optical system device according to an embodiment of the present invention.

A previously determined kind of biological material is immobilized at a preset position on the surface of the substrate, and at any (one or more) of immobilized positions of the biological materials, a target biological material labeled by a predetermined optical labeling element can be coupled. The shape of the substrate is, for example, as shown in FIG. 3, a string shape wound around a core 12.

The pipette tip 2 includes a large diameter portion 13 capable of storing the substrate, and a small diameter portion 14 leading to the large diameter portion 13 under the large diameter portion 13. The upper part of the large diameter portion 13 is detachably attached to a nozzle 5 of the pressure adjusting unit for sucking and discharging liquid through the small diameter portion 14.

The mechanical section 4 is provided above the optical information reader 3, and an operating plate 6 is provided in a border between these. A hole 7 through which the pipette tip 2 can pass, is provided in the operating plate 6. When the substrate stored in the pipette tip 2 is measured, the pipette tip 2 can be dropped so that the pipette tip 2 passes through the hole 7 and is positioned in the optical information reader 3.

On the operating plate 6, there are provided a container (not shown) storing various reagents used for the processing of the substrate, and a tip storing unit which stores unused pipette tips 2, with the large diameter portion 13 being directed upward, in such a state that the tip end of the nozzle 5 is inserted into the pipette tip 2, thereby enabling automatic installation of the pipette tip 2 to the nozzle 5. A used tip discharging unit for storing used pipette tips 2 automatically detached from the nozzle 5, may be provided on the operating plate 6.

The optical information reader 3 is provided below the operating plate 6 in such a state that the entire optical information reader 3 is housed in a shielding housing 8 that can shield the light from the outside.

The entire mechanical section 4 is covered with a cover 9 having a window enabling monitoring from outside. The mechanical section 4 has as mechanisms for moving the pipette tip 2 itself in the vertical direction; a support 50 which supports the pipette tip 2 and the nozzle 5 to which the pipette tip 2 is attached, a slider 51 connected to the support 50, and a cylindrical guide member 52 which guides the slider 51, and hence, the support 50 movably along the Z axis direction. The guide member 52 is provided so as to be suspended from above by the XY-axis moving unit (not shown) for moving the pipette tip 2, the nozzle 5, and the support 50 in the XY axis direction.

A connecting bar 53 is provided on the slider 51, and is connected to a nut 55 which is screwed together with a ball screw 54. The ball screw 54 is coupled with a shaft of a motor 57 via a coupling portion 56, and is rotated by the motor 57. Accordingly, the nut 55, and hence, the pipette tip 2 coupled therewith are moved up and down. The support 50, the slider 51, the guide member 52, and the ball screw 54 correspond to the Z-axis moving unit.

A cylinder (not shown) which communicates with the nozzle 5, is provided on the support 50. The nozzle 5 is rotatably connected to the cylinder. A guide member 58 is fixed to the support member 50, and guides so that the slider 59 for sliding a plunger (not shown) along the Z axis direction, can slide in the cylinder. A ball screw mechanism or the like (not shown) for driving the slider 59 in the Z axis direction, is provided on the support 50. The nozzle 5, the cylinder, the plunger, and the slider 59 correspond to the pressure adjusting unit.

In FIG. 1, reference symbol 60 denotes a motor for rotating the nozzle 5, that is, the pipette tip 2 along the axis thereof. The rotation is transmitted to a toothed pulley 61 of the nozzle 5 by a toothed pulley (not shown) or the like provided on the rotation shaft of the motor 60. The motor 60 and a rotation mechanism driven by the motor 60 are fitted to the support 50 via a bracket 62. The motor 60, the toothed pulley 61, the bracket 62, and the like, correspond to the rotation scanning unit. The combination of the rotation scanning unit and the Z-axis moving unit correspond to the scanning unit.

The mechanical section 4 is further provided with a punching pin 63 for punching a thin film covering an opening of the container (not shown) provided on the operating plate 6 in order to prevent evaporation of the liquid stored in the container, which can move up and down in the axial direction of the nozzle 5 by a shaft 64 linked with the plunger in the cylinder.

In the figure, reference symbol 65 denotes a power circuit, 66 denotes a fan 66 for feeding air to the power circuit 65, and 67 denotes a duct for exhausting the air introduced into the power circuit 65 to the outside.

The optical information reader 3 will be described with reference to FIG. 2.

The optical information reader 3 has a mechanical section 43 for reading optical information, being a mechanical part of the optical information reader 3, and an optical system housing unit 97, being an optical part.

The mechanical section 43 for reading optical information can be divided into; a mechanism which rotatably receives the respective set-of-six pipette tips 2 detachably attached to the set-of-six nozzles 5 at a predetermined height position, by means of the Z-axis moving unit in the mechanical section 4, and a mechanism for measurement in order to obtain the optical information from the substrate stored in the received pipette tips 2.

The part which rotatably receives the respective pipette tips 2 includes a receiving tube 69 which comes in contact with the outer circumference of a part of a cone portion 68 between the large diameter portion 13 and the small diameter portion 14 of the pipette tip 2 so as to keep the rotation axis of the pipette tip 2 from moving, and a set-of-six bearing units 71 including a bearing 70 fitted to the outside face of the tube 69. The respective set-of-six bearing units 71 are connected to a slider 73 capable of sliding in the Z axis direction along a shaft 72. The slider 73 is resiliently supported in a state energized upward by a compression spring 74 provided so as to surround the shaft 72 below the slider 72. A base 75 on which the shaft 72 is fixed is provided below the compression spring 74. A light shielding plate 76 is provided on the slider 73, and a micro photo sensor 77 formed of a photodetector and a light emission element, is fitted to a sensor bracket 78 secured on the base 75. The position of the bearing portion 71, that is, the position of the pipette tips 2, can be set to a position at which the optical information can be read, by shielding or not shielding between the photodetector and the light emission element by the light shielding plate 76.

A head 80 having a built-in optical system device such as a lens, with a focal length thereof being adjusted so as to be able to receive the light from respective stored substrates 11 and from predetermined positions on the respective substrates 11, is provided with an end face thereof being away from the large diameter portion 13 by a predetermined distance, in order to obtain the optical information on the respective substrates 11 stored in the respective large diameter portions 13 of the respective pipette tips 2. An arm 79 protrudes forward from the head 80, and a positioning roller 81, which comes in contact with the side of the large diameter portion 13 of the pipette tip 2, is rotatably supported at the end of the arm 79, thereby maintaining the predetermined distance between the head 80 and the pipette tip 2, and enabling transmission of vibrations due to rotation about the axis of the pipette tip 2 to the head 80. An optical fiber 16 is detachably connected to the back of the head 80 via a connector 82.

The head 80 corresponds to the light-receiving end 15. The head 80 is fitted to a gonio stage 83 so as to be able to adjust the angle (elevation or dip) of the head 80 on a vertical plane including a center of the axis of the pipette tip 2 or parallel to the center of the axis. The angle can be adjusted by an adjusting screw 84. The head 80 and the gonio stage 83 are fitted to an XY axis direct-acting section 85. The XY axis direct-acting section 85 can move a slight distance in either an X-axis direction (front-back direction of the page) or a Y-axis direction (left and right direction on the page). The XY axis direct-acting section 85 includes a Y axis direct-acting section 86 formed of a fixed part and a movable part which smoothly moves a slight distance in the Y-axis direction relative to the fixed part, and an X axis direct-acting section 87 formed of a movable part, to which the fixed part of the Y axis direct-acting section 86 is fitted, which smoothly moves a slight distance in the X-axis direction relative to the fixed part. Reference symbols 88 and 89 denote stoppers which stop movement of the respective movable parts by engaging with the respective fixed parts. The gonio stage 83 and a fiber supporting bracket 90 are fitted to the movable part of the Y axis direct-acting section 86 of the XY axis direct-acting section 85. A pressing portion 91, which resiliently presses the optical fiber 16 from upper and lower sides, is provided at one end of the fiber supporting bracket 90.

The entire XY axis direct-acting section 85 is fixed to a movable part of an XY axis direct-acting section 92, which can move along the X axis, being the array direction of the set-of-six pipette tips, so that the entire set-of-six pipette tips 2 can be measured. The light shielding plate 93 for performing positioning in the X-axis direction, is provided on the movable part of the X axis direct-acting section 92, such that the light shielding plate 93 can shield between the photodetector and the light emission element of the micro photo sensor 94. The fixed part of the X axis direct-acting section 92 is fixed on a bottom plate 95 of the apparatus. The X axis direct-acting section 92 is driven by a motor 96 in the X-axis direction.

The optical system housing unit 97 includes a first optical system device 18 and a second (third) optical system device 44 (45), and the optical system device 18 is detachably connected to the optical fiber 16 via a connector 17. The combination of the optical system devices 18, 44 and 45 correspond to the optical information measuring unit. The optical fiber 16 corresponds to the optical waveguide. The pipette tip 2, the light-receiving end 15, the mechanical section 43 for reading optical information, the optical information measuring unit, an information processor 40, an input and display unit 41, and an output unit 42 correspond to the optical information reader 3.

The optical system of the optical information reader 1 will be described with reference to FIGS. 3, 4, and 5.

In the embodiment, a case will be described in which a first fluorescent material Cy5 and a second fluorescent material Cy3 are used as the optical labeling element, to label the target biological material by making the ratio of quantity different from each other, and when a target biological material is coupled with the biological materials immobilized on the substrate, and there is the optical labeling element on the substrate, the optical information is read from the optical labeling element on the substrate.

An optical system for reading the optical information when the first optical system device 18 is used as the optical information reader 1 according to the embodiment will be described with reference to the block diagram shown in FIG. 3. The optical system device 18 is used when the first fluorescent material Cy5 and the second fluorescent material Cy3 are specified as the measuring object. The optical information reader 1 includes: the nylon string substrate 11 spirally wound around the surface of a resin columnar core 12 and put in the large diameter portion 13 of one of the set-of-six pipette tips 2; one of the light-receiving ends 15 provided at a position at which the light from the substrate 11 can be received; the optical system device 18 which houses various types of optical system parts for obtaining the optical information by introducing the light received by the light-receiving end 15 into a housing unit 18a which shields light from the outside other than the received light; the mechanical section 43 for reading optical information for relatively changing the position of the light-receiving end 15 relative to the substrate 11; the mechanical section 4; the information processor 40 which obtains the optical information based on the electric signal from the optical system device 18, the mechanical section 43 for reading optical information, and the mechanical section 4, and gives instruction to these devices; the input and display unit 41 formed of a liquid crystal display, a keyboard, a mouse and the like, which inputs various types of data to the information processor 40, gives instructions, or displays instruction information and the optical information; and an output unit 42 such as a printer, a communication unit, a CD driver, a flexible disk driver, which outputs processing results of the information processor 40.

The light-receiving end 15 is connected to the connector 17 provided on a wall of the housing unit 18a via the optical fiber 16. The optical system device 18 is provided with four photomultipliers 19, 20, 21, and 22 corresponding to the photoelectric element. Here the photomultipliers 19 and 21 are for measuring the first fluorescent material Cy5 of the optical labeling element, which is one of the specific measuring objects, and are set so that the multiplication factor serving as the characteristic of respective photomultipliers 19 and 21 becomes different corresponding to the measuring object.

The photomultipliers 20 and 22 are for measuring the second fluorescent material Cy3 of the optical labeling element, which is another specific measuring object, and are set so that the multiplication factor serving as the characteristic of respective photomultipliers 20 and 22 becomes different corresponding to the measuring object.

The optical system device 18 also includes a laser light source 23 having a wavelength of 532 nm, and a laser light source 24 having a wavelength of 635 nm as a substrate irradiation unit, and laser beams are irradiated to the respective immobilized positions on the substrate 11 via the optical system at the light-receiving end 15. The laser light source 23 is for pumping the second fluorescent material Cy3 (pump light of 550 nm with maximum absorption, and pump light of 514 to 565 nm with 50% absorption). The laser light source 24 is for pumping the first fluorescent material Cy5 (pump light of 649 nm with maximum absorption, and pump light of 629 to 669 nm with 50% absorption). The optical system device 18 is further provided with a plurality of lenses 25, 32, 33, 37, and 38. The optical system device 18 further includes a dichroic long pass filter 26 which transmits light of 560 nm or more and reflects light less than 560 nm, a dichroic long pass filter 27 which transmits light of 610 nm or more and reflects light less than 610 nm, and a dichroic long pass filter 28 which transmits light of 650 nm or more and reflects light less than 650 nm. The optical system device 18 further includes a 695/55 band pass filter 29 which transmits light of total width of 55 nm centering on 695 nm, a long pass filter 30 which transmits light of 660 nm or more, a 580/30 band pass filter 34, a long pass filter 35 which transmits light of 560 nm or more, a mirror 39, and half mirrors 31 and 36. Here, the 695/55 band pass filter 29 indicates that the total bandwidth is 55 nm and the central wavelength thereof is 695 nm, and the 580/30 band pass filter 34 indicates that the total bandwidth is 30 nm and the central wavelength thereof is 580 nm.

The light transmitted through the lens 25, the dichroic long pass filters 26, 27, and 28, the 695/55 band pass filter 29, and the long pass filter 30, that is, the light of equal to or more than 677.5 nm and less than 722.5 nm, of the light received via the connector 17, is input to the photomultipliers 19 and 21. Since a part of the wavelength of the first fluorescent material Cy5 (fluorescent wavelength with maximum absorption is 670 nm, and fluorescent wavelength with 50% absorption is 655 to 692 nm) is included in this range, fluorescence from the first fluorescent material as the specific measuring object is transmitted to both the photomultipliers 19 and 21.

On the other hand, the light transmitted through the lens 25 and the dichroic long pass filter 26, reflected by the dichroic long pass filter 27, and transmitted through the 580/30 band pass filter 34 and the long pass filter 35 which transmits light of 560 nm or more, that is, the light of equal to or more than 565 nm and less than 595 nm, of the light received via the connector 17, is input to the photomultipliers 20 and 22. Since the wavelength of the second fluorescent material Cy3 (fluorescent wavelength with maximum absorption is 570 nm, and fluorescent wavelength with 50% absorption is 556 to 588 nm) is included in this range, fluorescence from the second fluorescent material as the specific measuring object is transmitted to both the photomultipliers 20 and 22.

The laser beams having a wavelength of 532 nm from the laser light source 23 is reflected by the dichroic long pass filter 26, and irradiates the substrate 11 from the light-receiving end 15 via the connector 17, to pump the second fluorescent material. The laser beams having a wavelength of 635 nm from the laser light source 24 is reflected by the dichroic long pass filter 28, and irradiates the substrate 11 from the light-receiving end 15 via the connector 17, to pump the first fluorescent material.

The signals obtained by converting electric signals from the photomultipliers 19, 20, 21, and 22 by an A/D converter, are input to the information processor 40, and the signals converted by the A/D converter are transmitted according to an instruction from the input and display unit 41. The information processor 40 sends an output instruction signal for the laser beams to the laser light sources 23 and 24, based on the instruction from the input and display unit 41. The information processor 40 can further control the pressure adjusting unit, the Z-axis moving unit, and the XY-axis moving unit in the mechanical section 4, the scanning unit, and the X axis direct-acting section 92 in the mechanical section 43 for reading optical information, based on the instruction from the input and display unit 41. Moreover, the information processor 40 can obtain information such as light-emitting position, immobilized position, shape of the substrate, scanning distance, scanning position, and immobilized position, by receiving signals from the mechanical section 4 and the mechanical section 43 for reading optical information.

Next an optical system using a second optical system device 44 according to the embodiment will be described with reference to FIG. 4.

In the embodiment, the first fluorescent material Cy5 serving as the optical labeling element is designated as the specific measuring object, while the second fluorescent material and the substrate 11 itself are designated as other measuring objects.

Parts the same as in FIG. 3 are denoted by the same reference symbols, and description is omitted.

The optical system parts of the second optical system device 44 according to the embodiment are different from those of the first optical system device 18 in FIG. 3 in that the fluorescence from the second fluorescent material is input to the photomultiplier 22, and the light from the substrate 11 is input to the photomultiplier 20. Therefore, a half mirror 36 which branches the received light to the photomultipliers 20 and 22 is provided before the received light is transmitted through the 580/30 band-pass filter 34 and the long pass filter 35. Accordingly, the light input to the photomultiplier 20 is light transmitted through the dichroic long pass filter 26 and reflected by the dichroic long pass filter 27, that is, light having a wavelength of equal to or more than 575 nm and less than 595 nm. The measuring object to be measured by the photomultiplier 20, is one for obtaining the optical information on the substrate 11 itself by inputting the laser beams of 532 nm output from the laser light source 23 and reflected by the substrate 11. Generally, due to the laser beams of 532 nm irradiated to the substrate 11, the light corresponding to the material is emitted from the substrate 11, and normally, it is a reflected wave of 532 nm having the same wavelength as that of an incident wave. The reflected light is shielded by the dichroic long pass filters 26 and 27, but it is not shielded 100 percent. In the embodiment, the light transmitted through the filter 26 without being shielded, and reflected by the filter 27 is used to obtain the optical information on the substrate 11 by the photomultiplier 20.

As the light input to the photomultiplier 22, the 580/30 band-pass filter 34 and the long pass filter 35 are provided in front of the photomultiplier 22, and the light transmitted through these filters 34 and 35 is input to the photomultiplier 22. The range of the wavelength of the light transmitted through these filters 34 and 35 is equal to or more than 575 nm and less than 595 nm. These filters 34 and 35 intercept the reflection light of 532 nm from the substrate 11, transmitted through the dichroic long pass filter 26 and reflected by the dichroic long pass filter 27, so that input of excess laser reflected light to the photomultiplier 22 can be restricted.

The optical information reader 1 using a third optical system device 45 according to the embodiment will be described with reference to FIG. 5.

Figure 4:
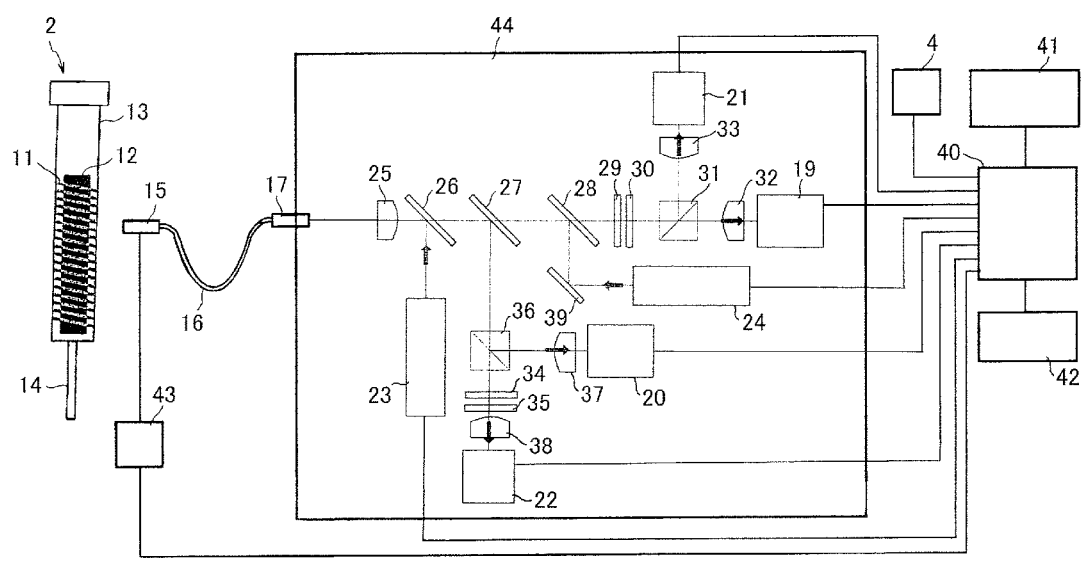
FIG. 4 is a conceptual diagram showing an optical system using a second optical system device according to an embodiment of the present invention.
Figure 5:
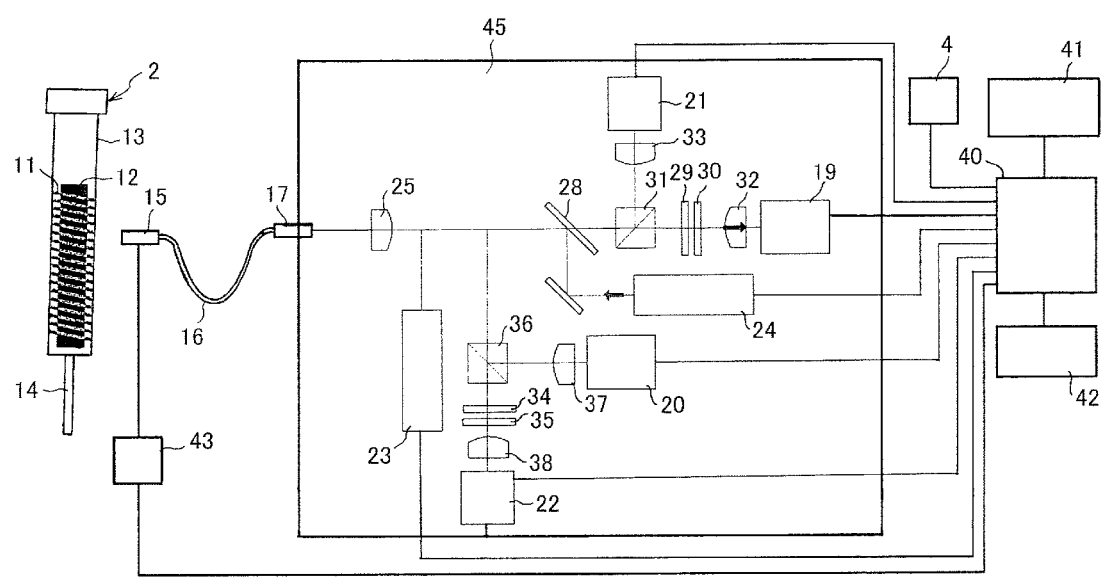
FIG. 5 is a conceptual diagram showing an optical system using a third optical system device according to an embodiment of the present invention.

Parts the same as in FIG. 3 or 4 are denoted by the same reference symbols, and description is omitted.

In the embodiment, the first fluorescent material Cy5 serving as the optical labeling element, and the substrate 11 itself are designated as other measuring objects.

The optical system parts of the optical system device 45 according to the embodiment are different from the optical system parts of the first and second optical system devices 18 and 44 in FIG. 3 or 4 in that the photomultipliers 20 and 22, and the laser light source 23 are not used, by removing the dichroic long pass filters 26 and 27. Moreover, by using the 695/55 band pass filter 29 and the long pass filter 30 which transmits the light of 660 nm or more between the half mirror 31 and the lens 32, the light transmitted through the dichroic long pass filter 28, which transmits light of 650 nm or more but reflects light less than 650 nm, is further narrowed down to light of equal to or more than 677.5 nm and less than 722.5 nm, to thereby take in the fluorescence of the first fluorescent material. On the other hand, the light of 635 nm irradiated from the laser light source 24 onto the surface of the substrate 11 and emitted from the substrate 11 (for example, reflected light of the same wavelength), and transmitted through the dichroic long pass filter 28 is restricted from being input to the photomultiplier 19. Furthermore, a part of the light emitted from the substrate 11 (for example, reflected light of the same wavelength) and transmitted through the dichroic long pass filter 28 is input to the photomultiplier 21 via the half mirror 31. The emitted light can be used in order to obtain optical information of the substrate 11 itself as the measuring object.

At this time, if the optical system device capable of setting two kinds of different multiplication factors as the characteristic of the photomultiplier 19 is to obtain an electric signal from the first fluorescent material every time the multiplication factor is changed, the electric signal on the first fluorescent material serving as the specified measuring object can be obtained by one photomultiplier 19.

If the half mirror 31 is also removed, and the 695/55 band-pass filter 29 and the long pass filter 30 are detachably provided, the one photomultiplier 19 can deal with a case in which the substrate 11 itself is the measuring object when a pair of filters 29 and 30 is detached, and the first fluorescent material is the measuring object when the filters 29 and 30 are attached.

The respective filters described above correspond to the light extraction unit for the respective measuring objects, for example, the first fluorescent material, the second fluorescent material, and the substrate 11 itself.

Next an operation of the optical information reader 1 according to the embodiment will be described.

Predetermined kinds of biological materials having a known structure corresponding to the content of the inspection are immobilized and arranged beforehand at predetermined positions on the string type substrate 11. For example, in an inspection for determining a base sequence of eighteen kinds of the target biological materials having eighteen kinds of unknown base sequences extracted from eighteen kinds of organisms, for example, a known oligonucleotide having various base sequences with a certain length is immobilized on the substrate 11 as the biological material.

After the substrate 11 on which the biological materials are arranged is stored in each of the six pipette tips 2 in a state in which the cores 12 wound with the string type substrate 11 are respectively fixed in the pipette tips 2, the six pipette tips 2 are engaged with and attached to the respective ends of the group-of-six nozzles 5 and mounted. On the other hand, a plurality of groups-of-six cassette type containers and microtiter trays are prepared on the operating plate 6, to store a solution containing three types of target biological materials, of 18 kinds of biological materials, in each container, suspended and labeled so as to be able to identify 18 kinds of target biological materials by coupling the first fluorescent material Cy5 and the second fluorescent material Cy3, and if necessary, another type of fluorescent material having a predetermined ratio of quantity, so as not to overlap in the same pipette tip 2. An opening of each container is covered with a film, and may be punched by the punching pin 63. Moreover a reagent suitable for promoting coupling by ligase between the target biological material in the solution and the biological materials immobilized on the substrate 11 is mixed in the solution. A cleaning solution, a measuring solution and the like are stored in other containers.

Next the set-of-six pipette tips 2 attached to the nozzles 5 are moved to the set-of-six container positions by the XY-axis moving unit (not shown) provided in the mechanical section 4, and each end of the pipette tips 2 is inserted into each container by the Z-axis moving unit. Then, the solution in which the labeled target biological materials are suspended is sucked by using the pressure adjusting unit, and brought into contact with the biological materials on the substrate 11 stored in the large diameter portion 13 of the pipette tip 2 to promote a reaction. After a predetermined time has passed, the solution sucked up to the large diameter portion 13 is discharged to the container, and then, the set-of-six pipette tips 2 are moved to a container position where the cleaning solution is stored, by the Z-axis moving unit and the XY-axis moving unit, to repeat suction and discharge of the cleaning solution, thereby removing the target biological material not coupled with the substrate 11.

The pipette tips 2 are then moved to a container in which the measuring solution is stored, and the measuring solution is sucked into the pipette tip 2. Here when the substrate 11 is optically measured from outside of the translucent pipette tip 2, the measuring solution can remove droplets and bubbles by filling the solution in between the substrate 11 and the pipette tips 2 in which each substrate 11 is stored, and can prevent the situation where the optical information becomes unclear due to refraction, reflection, or the like of light between the pipette tips 2 and the inner space thereof, by reducing a difference in the refractive index between the pipette tips 2 and the substrate 11 to the minimum.

After the pipette tips 2 are moved to the position of the hole 7 in the operating plate 6 by the XY-axis moving unit, the set-of-six pipette tips 2 are dropped all together, penetrating the hole 7, so as to be inserted into the housing 8 by the Z-axis moving unit.

Figure 2:
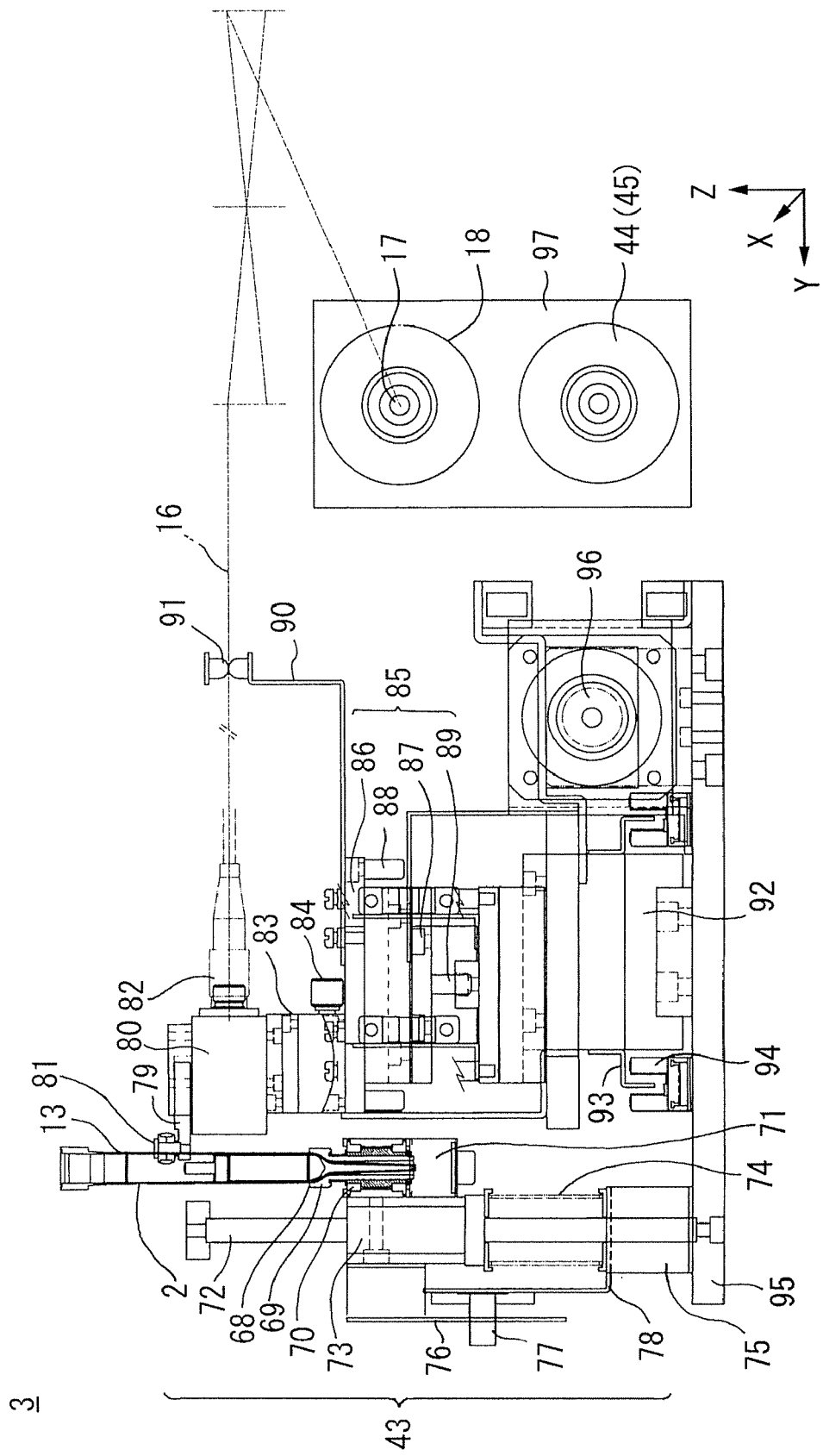
FIG. 2 is a side view showing the optical information reader according to the embodiment of the present invention.

As a result, as shown in FIG. 2, each small diameter portions 14 of the set-of-six pipette tips 2 is inserted into the receiving tube 69 of the bearing portion 71, and comes in contact with the outer circumference of the cone portion 68 of the pipette tip 2 in a state with the central axis of the receiving tube 69 coinciding with the central axis of the pipette tip 2. At this time, the first pipette tip 2 of the set-of-six pipette tips 2 is dropped by the Z-axis moving unit in a state with the positioning roller 81 provided on the head 80 coming in contact with the side of the large diameter portion 13 of the pipette tip 2, until the light-receiving end of the end face on the light receiving side of the head 80 is positioned immediately below the lower end of the core wound with the substrate 11 stored in the pipette tip 2. This state is detected since the micro photo sensor 77 is shielded by the light shielding plate 76.

Next the angle (elevation or dip) of the head 80 is manually adjusted by the adjusting screw 84, and adjustment from the center of the axis to the X direction or the Y direction is manually made by adjusting the XY axis direct-acting portion 85. At this time, the light receiving direction and the angular aperture of the head 80 relative to the substrate 11 are set so that light is received outside of the incident route and reflection route of the pump light determined based on the irradiation direction and the illuminating angle of the head 80 relative to the substrate 11, and the shape of the substrate 11. For this purpose, the angle of the head 80 is set so that the head 80 is at a predetermined angle (for example, an angle equal to or larger than the angular aperture) relative to a normal direction of the substrate 11 in a horizontal plane of the head 80.

Scanning is then performed by gradually dropping the pipette tip 2 by means of the Z-axis moving unit, while simultaneously rotating the relevant pipette tip 2 by the rotation scanning unit in the mechanical unit 4, and at the same time, the head 80 receives the light from the substrate 11, or irradiates the laser beams onto the substrate 11. At this time, since the head 80 comes in contact with the large diameter portion 13 of the pipette tip 2 by the positioning roller 81, slight movement of the pipette tip 2 is transmitted to the head 80, and the pipette tip 2 and the head 80 synchronize with each other. As a result, scanning is performed in a state with relative misregistration between the head 80 and the substrate 11 being suppressed to the minimum. That is, with regard to vibrations based on the characteristic frequency of the pipette tip 2 in which the substrate 11 is stored, and the characteristic frequency of the head 80, by making one of the characteristic frequencies follow the other, a difference between the both frequencies can be made equal to or less than a predetermined value. The optical information is input to the first optical system device 18, or the second (third) optical system device 44 (45) by the optical fiber 16 via the connector 82.

When the optical measurement for the first pipette tip 2 has finished, the head 80 and the like are moved to the position of the next pipette tip 2 in the arrangement of the set-of-six pipette tips 2 along the X axis by using the X axis direct-acting section 92, and the same processing is performed with respect to all of the set-of-six pipette tips 2.

Figure 6:
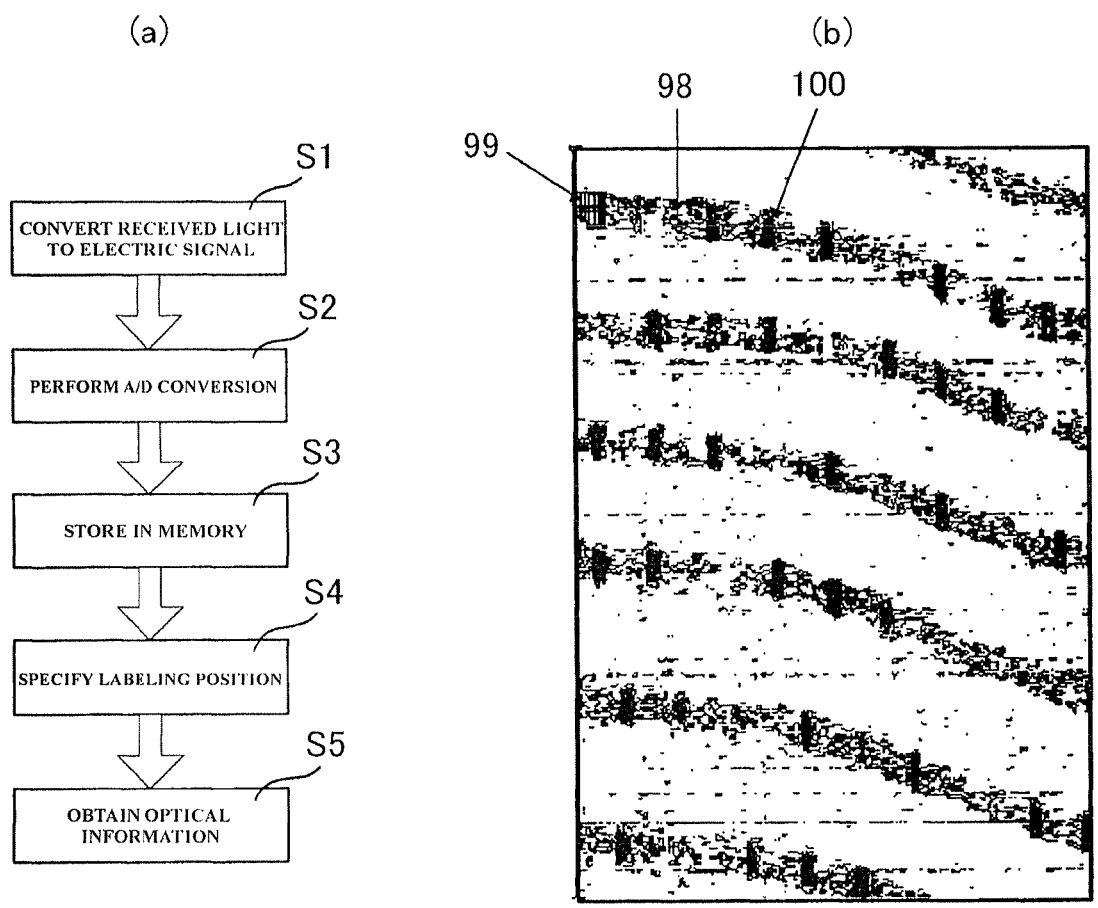
FIG. 6 is a flowchart of optical measurement and a measurement result according to the embodiment of the present invention.

Next processing of the optical information when the second optical system device 44 is used as the optical information reader 1 will be described with reference to FIGS. 4 and 6.

The head 80 is relatively moved approximately along the substrate 11, by dropping the pipette tip 2 while rotating the pipette tip 2 by means of the scanning unit. At this time, the laser light source 23 irradiates laser beams for pumping having a central wavelength of 532 nm through the head 80, and the laser light source 24 irradiates laser beams for pumping having a central wavelength of 635 nm through the head 80.

Upon irradiation of the pump light, when there is the first or the second fluorescent material on the substrate 11, the pumped fluorescence is input to the optical system device 44 via the light-receiving end 15 having the head 80, the optical fiber 16, and the connector 17. Even when there is no fluorescent material on the substrate 11, the pump light is input to the optical system device 44 via the light-receiving end 15, the optical fiber 16, and the like, together with the light reflected by the substrate 11. Of these lights, a part of the wavelength range of the fluorescence by the first fluorescent material Cy5 (for example, 649 nm with maximum absorption, and 629 to 669 nm with 50% absorption) is transmitted through the dichroic long pass filters 26, 27, and 28. This is because the transmission range thereof is equal to or more than 650 nm, and hence, overlaps on a part of the wavelength range of the fluorescence. In the optical system device 44 is also provided the 695/55 band-pass filter 29, and the long pass filter 30. Since the wavelength range by the filters 29 and 30 is equal to or more than 667.5 nm and less than 722.5 nm, the wavelength range of the fluorescence transmitted through the dichroic long pass filters 26, 27, and 28 can be narrowed down further, but the quantity of light to be input to the photomultipliers 19 and 21 can also be limited by the filters 29 and 30. Particularly, input of the pump light leaked from the light having a wavelength of 635 nm irradiated from the laser light source 24 onto the substrate 11, reflected, and transmitted through the dichroic long pass filters 26, 27, and 28, can be limited by the filters 29 and 30.

Accordingly, the fluorescence from the first fluorescent material Cy5, being the specified measuring object, can be input to both the photomultipliers 19 and 21. At this time, by making the respective characteristics, that is, the multiplication factor of the photomultipliers 19 and 21 different from each other, even if the quantity of light of the first fluorescent material varies, the quantity of light can be amplified by either one of the photomultipliers 19 and 21 without saturation, thereby enabling output of a relevant electric signal.

On the other hand, the second fluorescent material Cy3 is not the specific measuring object, but is a normal measuring object, and is measured by one photomultiplier 22. The filters 34 and 35 can limit the quantity of light of the pump light having a wavelength of 532 nm irradiated from the laser light source 23 onto the substrate 11 and reflected, which is input to the photomultiplier 22.

Moreover in the second optical system device 44 according to the embodiment, the substrate 11 is measured as the measuring object. Regarding the measuring object, the pump light of 523 nm output from the laser light source 23 is reflected by the substrate 11, transmitted through the filter 26, and reflected by the filter 27, and the light having a wavelength of 560 nm or more and less than 610 nm, is input to the photomultiplier 20 and converted to an electric signal.

Next is a description of the processing of the respective electric signals obtained by converting the light received by the optical system device 44. As shown in FIG. 6(a), in step S1, the light received by the optical system device 44 is converted to an electric signal by the respective photomultipliers 19, 20, 21, and 22.

In step S2, the electric signal converted by the respective photomultipliers 19, 20, 21, and 22 is converted to a digital signal by the A/D converter (not shown), and in step S3, the digital signal is temporarily stored in a memory area of the information processor 40 of the specified measuring object.

In step S4, the information processor 40 specifies the labeling position and the shape of the substrate 11, by calculation based on the level of the electric signal from the memory, the identification information of the photomultipliers 19, 20, 21, and 22 to which the electric signal is output, the acquisition time of the electric signal, and the scan position information based on the signal from the scanning unit.

In step S5, the optical information on the substrate 11 is obtained from the data relating to the substrate 11, based on the identification position and the shape of the substrate 11. The optical information obtained in this manner is shown in FIG. 6(b). Here, reference symbol 98 denotes the substrate 11, 99 denotes a marker indicating the reference position of the substrate 11, and 100 denotes the optical labeling element formed from the first fluorescent material. When it is determined that the predetermined route of the scan is along the substrate 11, the biological material with which the optical labeling element is coupled can be specified based on the order of the scan.

Figure 7:
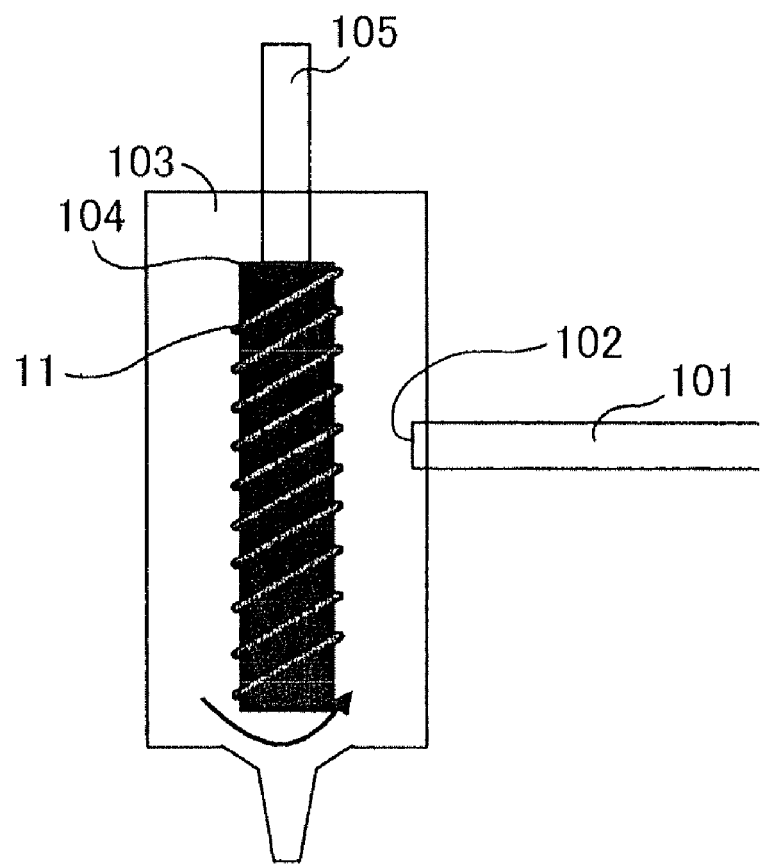
FIG. 7 is a conceptual diagram showing a relation between a substrate and light-receiving ends according to the embodiment of the present invention.

FIG. 7 shows a relation between the substrate 11 and the light-receiving end 101 in an optical information reader according to another embodiment.

In this optical information reader, an end 102 of the light-receiving end 101 having the optical fiber, is provided in a container 103 for housing the substrate 11, penetrating a wall thereof. In this example, the light-receiving end 101 is fixed to a stationary container 103. The substrate 11 is wound around a core 104, and the core 104 is fitted to a rotating shaft 105 concentrically provided. The rotating shaft 105 moves along the vertical direction, while rotating about the central axis. In this embodiment, the rotating shaft 105 corresponds to the scanning unit.

In this case, since the light-receiving end 101 is provided inside of the container 103, the light from the substrate 11 can be obtained more clearly, since the light need not be transmitted through the wall of the container 103.

The embodiments described above are for specifically explaining the present invention for clear understanding, and are not limiting to other embodiments. Accordingly, the embodiments can be modified without changing the purport of the invention. For example, the number of nozzles, and hence, the number of pipette tips are not limited to six, and may be other numbers, for example, 1, 2, 3, 4, 5, 7, and 8. The number of the photomultipliers is not limited to the number described above. Moreover, only the particular fluorescent materials are described as the optical labeling element, but other fluorescent materials, for example, organic substances such as fluorescein isothiocianate (FITC), rhodamine, isothiocianate, IRD40, and (Cy3 or Cy5), and inorganic substances which emit long lived fluorescence such as europium complex can be used. Furthermore, the optical labeling element can be not only fluorescent but also phosphorescent or chemiluminescent.

It has been described that the three types of optical system devices described above are independently provided, but another type of optical system device can be realized by using the one type of optical system device and providing the optical system parts removably, attachably, or movably from outside. Moreover, a plurality of light-receiving ends may be provided, so that each light-receiving end corresponds to a different optical system device.

Only a case in which the substrate is a string type has been explained, but the substrate may be another shape, for example, a plate shape or a thin film shape. In the above examples, only an oligonucleotide has been described as the biological material, but the present invention is not limited thereto, and for example, not only other genetic materials but also immunity substances, amino acids, proteins, and sugar chains can be used as the biological material.

The above respective components, parts, and devices, for example, the nozzle, the pipette tip, the light-receiving end, the photomultiplier, the lens, the filter, the mechanical section, and the optical information reader can be appropriately modified or changed and optionally combined.

INDUSTRIAL APPLICABILITY

The present invention relates to fields in which inspection, analysis, and assay on biological materials such as genetic materials, immunity substances, proteins, amino acids, hormones, fats, and sugar chains are required, for example, the engineering field, fields of foods, agricultural produce, livestock industry, and seafood processing, fields of pharmaceutical production, biochemistry, hygiene, health, immunization, infectious disease, and medical care, and chemical and biological fields.

EXPLANATION OF REFERENCE SYMBOLS

1 Optical information reader
2 Pipette tip
3 Optical information reading unit
4 Mechanical section
5 Nozzle
6 Operating plate
7 Hole
8 Housing
11 Substrate
12, 104 Core
13 Large diameter portion
15, 101 Light-receiving end (head 80)
16 Optical fiber (optical information measuring unit)
18, 44, 45 First, second, and third optical system device (optical information measuring unit)
43 Mechanical section for reading optical information
50 Support

The invention claimed is:

1. An optical information reader comprising:
a substrate on which one or more biological materials labeled by a combination of presence or extent of a plurality of kinds of optical labeling elements are immobilized at one or more different immobilized positions;
a light-receiving end capable of receiving light from said substrate;
an optical information measuring unit which obtains optical information on a specific measuring object on said substrate based on an electric signal obtained by converting the light received by said light-receiving end by a photoelectric element, which performs photoelectrical conversion according to different characteristics determined depending on said measuring object, said optical information measuring unit comprising a plurality of photoelectric elements having said different characteristics; and
a scanning unit which scans said substrate by effecting relative movement between said substrate and the light-receiving end;
a light distribution unit which extracts light from the light-receiving end, and simultaneously distributes the extracted light to each photoelectric element, the extracted light having a plurality of wavelength ranges, each wavelength range corresponding to a different measuring object on said substrate, each distribution of the extracted light to each photoelectric element corresponding to a different wavelength range; and an optical waveguide via which the light distribution unit extracts the extracted light from the light-receiving end, the optical waveguide extending from the light-receiving end;

wherein each photoelectric element comprises a plurality of photomultipliers, each plurality of photomultipliers having a different multiplication factor; and wherein the extracted light distributed to each photoelectric element is further distributed between the photomultipliers thereof.

2. An optical information reader according to claim 1, wherein said optical information measuring unit comprises;

a connector detachably connected to said light-receiving end via said optical waveguide, and a light extraction unit which extracts a wavelength range corresponding to said measuring object, and said photoelectric element is two or more photomultipliers, for which a multiplication factor corresponding to the measuring object on said substrate is set.

3. An optical information reader according to claim 1, wherein said optical labeling element includes one which emits light by irradiating pump light, and said optical information measuring unit has an irradiation unit which irradiates said pump light onto said substrate.

4. An optical information reader according to claim 3, wherein a light-receiving direction and an angular aperture of said light-receiving end relative to said substrate is set so that said light-receiving end receives light from said substrate, outside of an incident route and a reflection route of said pump light determined based on an irradiation direction and an illuminating angle of said irradiation unit relative to said substrate, and a shape of said substrate.

5. An optical information reader according to claim 3, wherein an illuminating angle formed between the optical axis of said irradiation unit and a normal at a measuring position on the substrate is larger than an angular aperture of said light-receiving end relative to the measuring position on the substrate.

6. An optical information reader according to claim 3, wherein said irradiation unit irradiates light using an optical system at said light-receiving end.

7. An optical information reader according to claim 1, wherein said optical information measuring unit recognizes the shape of said substrate based on the light both from said optical labeling elements on said substrate and said substrate itself, as said measuring objects, received by said light-receiving end.

8. An optical information reader according to claim 1, wherein said substrate or said light-receiving end rotates relatively to an axis passing through the center of the substrate, and also moves relatively to the axial direction, thereby spirally scanning a measurement area to be measured by said optical information measuring unit, to obtain the optical information.

9. An optical information reader according to claim 1, wherein said scanning unit scans the substrate based on the specified shape of the substrate, and said optical information measuring unit obtains the optical information based on the specified shape of the substrate.

10. An optical information reader according to claim 9, wherein said scanning unit scans along a predetermined route set on said substrate, and said optical information measuring unit obtains the optical information based on the order of scanning of said optical labeling elements.

11. An optical information reader according to claim 1, wherein said optical information measuring unit measures said substrate and the optical labeling elements of said biological materials individually.

12. An optical information reader according to claim 1, comprising a container for storing said substrate together with liquid, wherein receiving of light from said substrate by said light-receiving end is performed in a state with said substrate being stored in said container together with the liquid.

13. An optical information reader according to claim 12, wherein light between said optical information measuring unit and said optical labeling element or the substrate is transmitted without penetrating said container.

14. An optical information reader according to claim 1, wherein the immobilized positions of respective biological materials on said substrate are arranged according to a predetermined positional rule.

15. An optical information reader according to claim 1, wherein said optical waveguide of said optical information measuring unit is an optical fiber which transmits the light between said light-receiving end and said optical information measuring unit.

16. An optical information reader according to claim 1, wherein the optical information measuring unit performs photoelectrical conversion according to different characteristics determined depending on any one selected from a group consisting of emission intensity, reflected light intensity, emission wavelength, wavelength of reflected light, absorption wavelength, absorption intensity, emission lifetime, emission timing of said measuring object, and the shape of the measuring object; and wherein the measuring object is any one selected from a group consisting of the substrate, respective biological materials immobilized on the substrate, the optical labeling element, a marker as a reference of position on the substrate and a specific labeling material in the optical labeling element.

17. An optical information reader comprising:

a substrate on which one or more biological materials labeled by a combination of presence or extent of a plurality of kinds of optical labeling elements are immobilized at one or more different immobilized positions;

a light-receiving end capable of receiving light from said substrate;

an optical information measuring unit which obtains optical information on a specific measuring object on said substrate based on an electric signal obtained by converting the light received by said light-receiving end by a photoelectric element, which performs photoelectrical conversion according to different characteristics determined depending on said measuring object, said optical information measuring unit comprising an optical waveguide extending from the light-receiving end; and a scanning unit which scans said substrate by effecting relative movement between said substrate and the light-receiving end said scanning unit comprising a synchronization unit which applies vibrations based on a characteristic frequency of said substrate and a characteristic frequency of said light-receiving end to one of said substrate or the light-receiving end, so that the one follows the other, thereby making a difference between the characteristic frequencies thereof equal to or less than a predetermined value, wherein the optical information measuring unit further comprises a light distribution unit which extracts light from the light-receiving end via the optical waveguide and simultaneously distributes the extracted light between a plurality of photoelectric elements, the extracted light having a plurality of wavelength ranges, each wavelength range corresponding to a different measuring object on said substrate, each distribution of the extracted light to each photoelectric element corresponding to a different wavelength range;

wherein each photoelectric element comprises a plurality of photomultipliers, each plurality of photomultipliers having a different multiplication factor; and wherein the extracted light distributed to each photoelectric element is further distributed between the photomultipliers thereof.

18. An optical information reader according to claim 17, wherein said synchronization unit has a positioning part coming in contact with said substrate and said light-receiving end.

19. An optical information reader according to claim 18, wherein said positioning part comprises a rotor.

20. An optical information reader comprising:
   a substrate on which one or more biological materials labeled by a combination of presence or extent of a plurality of kinds of optical labeling elements are immobilized at one or more different immobilized positions;
   a light-receiving end capable of receiving light from said substrate;
   an optical information measuring unit which obtains optical information on a specific measuring object on said substrate based on an electric signal obtained by converting the light received by said light-receiving end by a photoelectric element, which performs photoelectrical conversion according to different characteristics determined depending on said measuring object; and
   a scanning unit which scans said substrate by effecting relative movement between said substrate and the light-receiving end,
   wherein said optical information measuring unit has: an optical waveguide extending from the light-receiving end, and also has a container for storing said substrate together with liquid, and receiving of light from said substrate by said light-receiving end is performed in a state with said substrate being stored in said container together with the liquid, and said light-receiving end is provided so as to penetrate said container and reach the inside or the inner wall of said container,
   wherein the optical information measuring unit further comprises a light distribution unit which extracts light from the light-receiving end via the optical waveguide, and simultaneously distributes the extracted light between a plurality of photoelectric elements, the extracted light having a plurality of wavelength ranges, each wavelength range corresponding to a different measuring object on said substrate, each distribution of the extracted light to each photoelectric element corresponding to a different wavelength range;
   wherein each photoelectric element comprises a plurality of photomultipliers, each plurality of photomultipliers having a different multiplication factor; and
   wherein the extracted light distributed to each photoelectric element is further distributed between the photomultipliers thereof.

* * * * *